(12) United States Patent
Karlsson et al.

(10) Patent No.: US 7,563,587 B2
(45) Date of Patent: Jul. 21, 2009

(54) METHOD AND KIT FOR CELL ANALYTE ASSAY

(75) Inventors: Robert Karlsson, Uppsala (SE); Pascale Richalet-Secordel, Weston, VT (US)

(73) Assignee: GE Healthcare Bio-Sciences AB, Uppsala (SE)

( * ) Notice: Subject to any disclaimer, the term of this patent is extended or adjusted under 35 U.S.C. 154(b) by 707 days.

(21) Appl. No.: 10/815,166

(22) Filed: Mar. 31, 2004

(65) Prior Publication Data

US 2004/0248213 A1    Dec. 9, 2004

Related U.S. Application Data

(60) Provisional application No. 60/460,539, filed on Apr. 4, 2003.

(30) Foreign Application Priority Data

Apr. 10, 2003 (SE) .................... 0301058

(51) Int. Cl.
*G01N 33/543* (2006.01)
(52) U.S. Cl. .......... 435/7.95; 435/7.1; 435/7.2; 435/286.5; 435/287.2; 435/973; 436/517; 436/518; 436/536; 436/537; 436/164; 422/82.05; 422/82.11
(58) Field of Classification Search .......... 436/518, 436/524, 525, 527, 528, 529, 530, 531, 164, 436/805, 819; 435/7.1, 7.2, 7.92–7.95, 286.5, 435/287.2, 973; 356/317, 318, 445; 422/82.05, 422/82.11
See application file for complete search history.

(56) References Cited

U.S. PATENT DOCUMENTS

| 4,659,678 A | | 4/1987 | Forrest et al. ............. 436/512 |
|---|---|---|---|
| 5,492,840 A | * | 2/1996 | Malmqvist et al. ......... 436/518 |
| 6,495,333 B1 | * | 12/2002 | Willmann et al. ......... 435/7.24 |

FOREIGN PATENT DOCUMENTS

| FR | 2 634 891 | | 2/1990 |
|---|---|---|---|
| WO | WO 90/05305 | | 5/1990 |
| WO | WO 96/38729 | * | 12/1996 |
| WO | WO 00/39580 | | 7/2000 |
| WO | WO 02/080647 A2 | | 10/2002 |

OTHER PUBLICATIONS

Fahraeus, R., et al., "The Viscosity of the Blood in Narrow Capillary Tubes" American Journal of Physiology; 1931; 96; 562-568.

\* cited by examiner

*Primary Examiner*—Gailene R Gabel
(74) *Attorney, Agent, or Firm*—Yonggang Ji

(57) ABSTRACT

The present invention relates to a method for analysing a cell sample for cell surface-bound or intracellularly bound analytes by providing an array of immobilised specific binding agents for a set of different ligands, where each ligand is specific to a respective cell surface-bound or intracellularly bound analyte, and using the array and the set of ligands in an inhibition type or a direct type assay format to determine cell surface-bound or intracellularly bound analytes in the cell sample. The invention also relates to assay kits for cell characterization.

6 Claims, 2 Drawing Sheets

METHOD AND KIT FOR CELL ANALYTE ASSAY

CROSS-REFERENCE TO RELATED APPLICATIONS

This application claims the benefit of U.S. Provisional Patent Application No. 60/460,539, filed Apr. 4, 2003; and also claims priority to Swedish Patent Application No. 0301058-4, filed Apr. 10, 2003; both of these applications are incorporated herein by reference in their entireties.

BACKGROUND OF THE INVENTION

1. Field of the Invention

The present invention relates to a method of analysing a cell sample for cell surface-bound and intracellularly bound analytes as well as to a kit for cell characterisation.

2. Description of the Prior Art

The cell walls of living organisms expose a number of cell surface elements of different functions such as, for example, receptors that interact with specific signal species in the cell environment, and antigens having specific immune reactions. Information on the presence and concentration of such surface elements in a cell sample is sought for various reasons. For instance, many disease states in particular animals, such as humans, have a genetic basis and can be characterised by changes in the patterns or levels of expression of various genes. Some of the genetic changes are expressed by alterations in cell surface antigens. For example, leukemia may be diagnosed on the basis of expression of specific CD, lymphoid and myeloid antigens.

An assay device based on cell surface antigen determination is disclosed in WO 00/39580. The assay device comprises an array of different molecules having a binding partner in a biological sample, wherein the pattern of binding of the binding partners, which may be cells or components released by the cells, to the respective molecules on the array provides an indication of a normal condition or disease condition or a propensity therefor to develop in an animal, avian or plant species, or the presence of a particular cell type or microbial, viral, parasitic or other pathogenic agent.

WO 96/38729 discloses the use of an inhibition type immunoassay to detect pathogens in a sample suspension. The suspension is first reacted with a predetermined excess of antibodies against the pathogen, and all pathogens are then removed from the suspension, e.g., by filtration or centrifugation. The amount of antibody in the resulting pathogen-free solution is then determined by contacting the solution with a sensor surface having immobilised receptor to the antibody.

WO 90/05305 discloses the use of bifunctional molecules for functionalising sensing surfaces. Each bifunctional molecule has a function for immobilizing the molecule to the sensing surface, and a bioselective function for interaction with a target biomolecule.

It is an object of the present invention to provide an improved array-based method for determining cell surface elements and/or intracellular components.

BRIEF SUMMARY OF THE INVENTION

The above and other objects and advantages are obtained by a novel method for analysing a cell sample for cell surface-bound analytes as well as intracellularly bound analytes. The method is based on contacting the cell sample with multiple ligands specific to different receptors on or within the cell, wherein each ligand in addition to the cell-specific part comprises a portion specifically binding to a particular member of an array. The ligands may be bound to the array after (inhibition assay) or before (direct assay) the contacting with the cell sample. This approach eliminates the need for purification of cell receptor molecules and the immobilization thereof to sensor surfaces as well as the often problematic regeneration of such receptor-supporting surfaces.

In one aspect, the present invention therefore provides a method for analysing a cell sample fluid for cell surface-bound and/or intracellularly bound analytes. In one embodiment, this method comprises the steps of:

(i) providing a solid support having on a surface thereof a plurality of different binding agents immobilized at defined positions on the surface, wherein each binding agent comprises one member of a specific binding pair;

(ii) contacting the solid support surface with a set of different ligands, each ligand comprising a first part capable of specifically binding to a specific analyte selected from cell surface-bound analytes and intracellularly bound analytes of a defined cell type, and a second part which comprises the other member of each specific binding pair, such that each ligand binds through its specific binding pair part to a specific position on the solid support surface;

(iii) determining the amount of binding of each ligand to the solid support surface;

(iv) incubating a cell sample-containing fluid with a set of ligands identical to that in step (ii) to permit the ligands to bind to cell surface-bound or intracellularly bound analytes of cells present in the cell sample fluid;

(v) contacting the cell sample fluid with a solid support surface according to step (i), to permit ligands that have not bound to cell surface-bound or intracellularly bound analytes to bind to the solid support surface; and (vi) determining the amount of binding of each ligand obtained in step (v) and comparing that binding amount with the amount of binding of the same ligand obtained in step (iii), reduced binding in step (v) indicating the presence of ligand-specific cell surface-bound analytes or intracellularly bound analytes in the cell sample.

In another embodiment, the method comprises the steps of:

(i) providing a solid support having on a surface thereof a plurality of different binding agents immobilized at defined positions on the surface, wherein each binding agent comprises one member of a specific binding pair;

(ii) contacting the solid support surface with a set of different ligands, each ligand comprising a first part capable of specifically binding to a specific analyte selected from cell surface-bound analytes and intracellularly bound analytes of a defined cell type, and a second part which comprises the other member of each specific binding pair, such that each ligand binds through its specific binding pair part to a specific position on the solid support surface;

(iii) contacting a cell sample-containing fluid with the solid support surface resulting from step (ii) having the ligands bound thereto to permit cells or cell fragments in the sample to bind to ligands on the solid support surface through cell surface-bound or intracellularly bound analytes; and (iv) determining the binding of cell surface-bound or intracellularly bound analytes to each ligand on the solid support surface.

In another aspect, the present invention provides an assay kit for cell characterisation, which kit comprises:

(i) a solid support having on a surface thereof an array of different binding agents immobilised at defined positions on the surface, wherein each binding agent comprises one member of a specific binding pair; and (ii) a set of different ligands, each ligand comprising a first part capable of specifically binding to a specific analyte selected from cell surface-bound analytes and intracellularly bound analytes of a defined cell type, and a second part which comprises the other member of a respective one of the specific binding pairs, such that each ligand may bind through its specific binding pair part to a specific position on the solid support surface.

In still another aspect, the present invention provides an assay kit for cell characterisation, which kit comprises:

(i) a solid support having on a surface thereof an array of different binding agents immobilized at defined positions on the surface, wherein each binding agent comprises one member of a specific binding pair; and (ii) a set of binding elements, each of which comprises the other member of a respective one of the specific binding pairs and a reactive group that permits chemical coupling of the binding element to a ligand which is capable of specifically binding to a specific analyte selected from specific cell surface-bound analytes and intracellularly bound analytes of a defined cell type.

The above and other aspects of the invention will be evident upon reference to the accompanying drawings and the following detailed description.

DEFINITIONS

Figure 1:
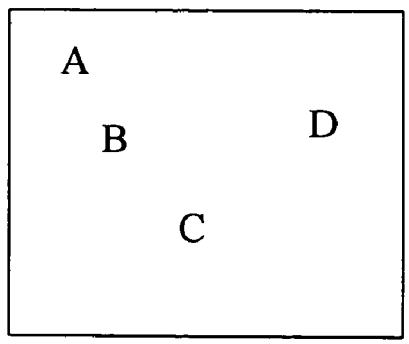
FIG. 1 is a schematic illustration of a solid support surface having an array of ligand binding agents immobilized thereto.

In describing and claiming the present invention, the following terminology will be used in accordance with the definitions set below.

"Array" and "array surface" as used herein are to be interpreted broadly and generally relate to a linear or two-dimensional array of discrete defined regions (here at least two), each having a finite area, formed on a solid support, usually on a continuous surface thereof, and supporting one or more binding agents. Ordered arrays of nucleic acids, proteins, small molecules, cells or other substances on a solid support enable parallel analysis of complex biochemical samples. In a "microarray", the density of discrete regions, or spots, is typically at least 100/cm$^2$, and the discrete regions typically have a diameter in the range of about 10-500 μm and are separated from other regions in the array by about the same distance.

"Defined region" as used herein relates to a localized area on the solid support surface. The defined region may have any desired shape, such as circular, rectangular, elliptical, etc, and is often referred to as a "spot".

"Solid support" as used herein is meant to comprise any solid (flexible or rigid) substrate onto which it is desired to apply an array of one or more binding agents. The substrate may be biological, non-biological, organic, inorganic or a combination thereof, and may be in the form of particles, strands, precipitates, gels, sheets, tubings, spheres, containers, capillaries, pads, slices, films, plates, slides, etc, having any convenient shape, including disc, sphere, circle, etc. The substrate surface supporting the array may have any two-dimensional configuration and may include, for example steps, ridges, kinks, terraces and the like and may be the surface of a layer of material different from that of the rest of the substrate.

"Specific binding pair" (abbreviated "sbp") as used herein describes a pair of molecules (each being a member of a specific binding pair) which are naturally derived or synthetically produced. One of the pair of molecules has a structure (such as an area or cavity) on its surface that specifically binds to (and is therefore defined as complementary with) a particular structure (such as a spatial and polar organisation) of the other molecule, so that the molecules of the pair have the property of binding specifically to each other. Examples of types of specific binding pairs (without any limitation thereto) are antigen-antibody, antibody-hapten, biotin-avidin, ligand-receptor (e.g., hormone receptor, peptide-receptor, enzyme-receptor), carbohydrate-protein, carbohydrate-lipid, lectin-carbohydrate, nucleic acid-nucleic acid (such as oligonucleotide-oligonucleotide).

"Nucleic acid" refers to a deoxyribonucleotide polymer (DNA) or ribonucleotide polymer (RNA) in either single- or double-stranded form, and also encompasses synthetically produced analogs that can function in a similar manner as naturally occurring nucleic acids. While natural nucleic acids have a phosphate backbone, artificial nucleic acids may contain other types of backbones, nucleotides or bases. These include, for instance, peptide nucleic acids (PNAs) as described in, e.g., U.S. Pat. No. 5,948,902 and the references cited therein; pyranosyl nucleic acids (p-NAs) as described in, e.g., WO 99/15540 (p-RNAs), WO 99/15539 (p-RNAs), and WO 00/11011 (p-DNAs); locked nucleic acids (LNAs), as described in, e.g., U.S. Pat. No. 6,316,198; and phosphothionates and other variants of the phosphate backbone of native nucleic acids.

"Oligonucleotide" refers to single stranded nucleotide multimers of from about 5 to about 100 nucleotides.

"Ligand" as used herein refers to a heterobifunctional molecule that, on one hand, has affinity for a given cell surface-bound or intracellularly bound analyte and, on the other hand, is capable of specifically binding to a moiety immobilized on a solid support. The ligand may be a naturally occurring molecule or one that has been synthesized.

"Antibody" as used herein means an immunoglobulin which may be natural or partly or wholly synthetically produced and also includes active fragments, including Fab antigen-binding fragments, univalent fragments and bivalent fragments. The term also covers any protein having a binding domain which is homologous to an immunoglobulin binding domain. Such proteins can be derived from natural sources, or partly or wholly synthetically produced. Exemplary antibodies are the immunoglobulin isotypes and the Fab, Fab', F(ab')$_2$, scFv, Fv, dAb, and Fd fragments.

"Hapten" as used herein means a low molecular species that may give rise to an immune response only when coupled to a larger molecule or cell or by aggregation. After immunisation, however, free haptens may react with antibodies.

"Cell surface analyte" as used herein refers to a molecule situated on the external surface of a cell. The cell surface analyte may be an antigen having a specific immune reaction. Cell surface antigens may, for example, consist of carbohydrates, lipids or proteins.

"Intracellularly bound analyte" as used herein refers to a molecule situated inside a cell and bound to an intracellular structure in such a way that it can not freely diffuse out of a cell wall that is permeable to specific binding partners. The intracellularly bound analyte may be an antigen having a specific immune reaction. Intracellularly bound analytes may, for example, consist of carbohydrates, lipids or proteins.

"Cell sample" as used herein means any sample of cells either from cell culture or isolated from an organism, an organ, a body liquid or a tissue. A cell sample preparation may be in the form of a suspension or adherent to a surface. The cell sample preparation may contain intact cells, or cells where the cell membrane has been rendered permeable so that specific binding partners to intracellular components can enter and leave the cell interior. This situation can for instance be achieved by fixation and permeabilization methods as described by Hedley, D. W., et al. in *Cytometry*, (*Communications in clinical cytometry*) 46:72-78 (2001).

The terms "set" and "plurality" as used herein, each means at least two.

In the specification and the appended claims, the singular forms "a", "an", and "the" are meant to include plural reference unless it is stated otherwise. Also, unless defined otherwise, technical and scientific terms used herein have the same meaning as commonly understood to a person skilled in the art related to the invention.

DETAILED DESCRIPTION OF THE INVENTION

As mentioned above, the present invention relates to a method of analysing a cell sample for a set of cell surface-bound analytes or intracellularly bound analytes as well as to an array surface that can be used therefor. Basically, the invention resides in (i) providing an array of immobilised specific binding agents for a set of different ligands, where each ligand is specific to a respective cell surface-bound or intracellularly bound analyte, and (ii) using the array and the set of ligands in either an inhibition type or a direct type assay format to determine cell surface-bound or intracellularly bound analytes in the cell sample. While the following description is primarily written with respect to cell surface-bound analytes, it is understood that the description is equally applicable to intracellularly bound analytes.

Figure 2:
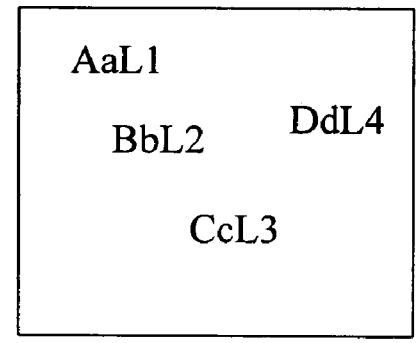
FIG. 2 is the array surface in FIG. 1 with ligands immobilized thereto.

An array surface for use in the invention may be constructed by immobilising to defined areas of a solid support surface a number of different ligand recognition elements, which for the sake of illustration are named A, B, C, D . . . , and each of which is one member of a specific binding pair. A schematic illustration of an array surface with immobilized recognition elements A, B, C, D . . . is shown in FIG. 1. The corresponding other members of these specific binding pairs, here named a, b, C, d . . . , are each attached (such as conjugated) to a respective one of a set of different ligands L1, L2, L3, L4 . . . , which are directed against specific surface structures or elements (such as, e.g., antigens) that may be present on the surface of a particular cell to form modified ligands aL1, bL2, cL3, dL4 . . . . The specific structures or elements on the cell surface are below often referred to as analytes. When the modified ligands are contacted with the array surface, aL1 combines with A on the surface, bL2 combines with B, etc, as is schematically illustrated in FIG. 2. The specific binding of a modified ligand to its recognition element on the array surface may be detected by a variety of different methods well known in the art as will be described in more detail below.

To carry out a study or "mapping" of a cell surface, the array surface is first contacted with the set of modified ligands aL1, bL2, cL3, dL4 . . . , each ligand preferably being at a certain known concentration, and the responses at the different recognition elements A, B, C, D . . . are measured. Usually, the array surface is then regenerated, i.e., the bound ligands are dissociated to expose the recognition elements A, B, C, D . . . . To permit such regeneration of the surface in a simple and general way, the binding between the modified ligands aL1, bL2, cL3, dL4 . . . and the respective recognition elements A, B, C, D . . . should be reversible.

Figure 3:
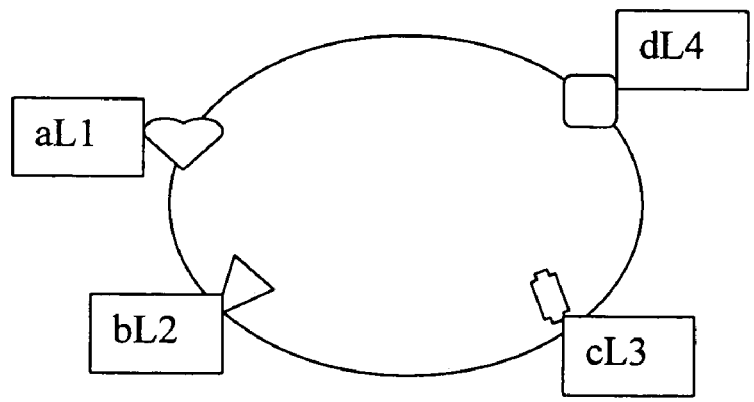
FIG. 3 is a schematic illustration of a cell having the same ligands as in FIG. 2 bound to different receptors on the cell surface.

Thereafter, preferably the same concentrations of ligands are incubated with a desired cell sample, which, for example, may be intact cells, expressing surface-bound analytes for the ligands aL1, bL2 etc. During the incubation, reactions will occur in solution and the ligands will bind to their respective cell surface analytes, as is schematically illustrated in FIG. 3. The sample solution is then brought in contact with the regenerated array surface which, as described above, permits self-orientation of free ligands in the solution. It is, however, not necessary to regenerate the array surface used for the initial binding of the ligands, but a separate identical array surface with recognition elements A, B, C, D . . . may optionally be used instead.

Preferably, however, prior to contacting the sample solution with the array surface, suspended or emulsified matter including cells, membranes etc are removed from the sample solution by, for instance, filtration or centrifugation. Alternatively, the sample solution may be passed over the array surface in a laminar flow that concentrates the suspended or emulsified matter in a central flow core spaced from the surface as described in WO 95/27208 (the disclosure of which is incorporated by reference herein). These procedures aim at separating free ligands aL1, bL2 etc from ligand(s) bound to cell surface specific analyte(s).

After the incubation of the cell sample with the ligand set, at least some of the different ligands will, depending on the presence and amount of corresponding cell surface analytes, be bound to the respective cell surface analytes, and optionally be removed along with the cells in the separation step. When the (optionally separated) cell sample solution is contacted with the array surface, the binding of the ligands aL1, bL2 etc to the corresponding recognition elements A, B etc on the array surface, will differ in rate and extent in comparison with the first-mentioned situation where the ligands were contacted with the array surface without preceding exposure to their respective cells surface analytes. Thus, when a difference (reduction) in the amount of binding of a specific ligand to the array surface is observed, this is an indication that the corresponding analyte was present in the cell sample. In this way at least a qualitative determination of cell surface analytes may be obtained.

As is readily recognised, repeating the above procedure with different concentrations of the cells or membranes in the cell sample (with intermediate regeneration of the array surface, or using additional identical array surfaces) may provide a quantitative measure of cell surface analytes in a cell sample, such as, e.g., the number of a particular receptor per cell.

Alternatively, rather than varying the concentration of the cell sample, the cell sample may be contacted with different concentrations of the ligands.

The procedure described above may thus be used to simultaneously determine or monitor a large number of cell surface-bound as well as intracellularly bound analytes and their concentrations.

I many cases, it may be advantageous to carry out the assay procedure in one or more flow cells (arranged in series or in parallel). Flow cell designs that may be contemplated are well known to the skilled person and need not be described herein. It is to be noted that an array may be distributed between two or more flow cells. For example, an array of eight ligands may be provided in, say, four flow cells, i.e., two ligands in each flow cell.

Alternatively to the inhibition type procedure described above, a direct type assay format may be used. In such a direct binding procedure, the array surface shown in FIG. 2, as obtained after contacting the surface with the set of modified ligands aL1, bL2, cL3, dL4 . . . , is brought in contact with the sample, which in this case also may be a cell lysate (in addition to intact or permeable cells) to permit cells or cell fragments to bind to ligands on the array surface through cell surface-bound analytes. The binding of cell surface-bound or intracellularly bound analytes to each ligand on the solid support surface is then determined.

Specific binding pairs Aa, Bb, Cc, Dd . . . that may be used are well known to the skilled person and may, for example, be hybridising strands of nucleic acids, usually oligonucleotides, one of the strands being linked (such as conjugated) to the ligands L1, L2, L3, L4 . . . . As another example may be mentioned antibodies or antibody fragments A, B, C, D . . . directed against haptens a, b, c, d . . . that are linked (such as conjugated) to the ligands L1, L2, L3, L4 . . . . Such heterobifunctional ligands and the preparation thereof are per se well known to the skilled person and need not be described any further herein.

As mentioned above, the members of the specific binding pairs preferably bind reversibly to each other, so that the array surface may regenerated in the sense that the surface-bound member is prepared for renewed binding of the other member of the binding pair. Conditions for cleaving or disrupting the binding between the members of each particular specific binding pair are well known to or may readily be established by the skilled person. For example, the strands of an oligonucleotide duplex may be separated at low or high pH conditions.

A kit for carrying out the above described assay procedure may comprise a sensor surface, such as a sensor chip, with immobilized recognition elements A, B, C, D . . . , and a set of corresponding cell surface antigen specific ligands aL1, bL2, cL3, dL4 . . . (or intracellularly bound antigen specific ligands).

Alternatively, the kit may comprise a sensor surface, such as a sensor chip, with immobilized recognition elements A, B, C, D . . . , and a set of corresponding binding elements a, b, c, d . . . that have been modified with a reactive group (e.g., succinimide ester, maleimide, dipyridyl-disulfide) so that they can readily be incorporated into ligands L1, L2, L3, L4 . . . of choice.

Exemplary cell types that may be of interest for use in the assay include: liver cells, gastrointestinal cells, epithelial cells, endothelial cells, kidney cells, cancer cells, blood cells, stem cells, bone cells, smooth muscle cells, striated muscle cells, cardiac muscle cells, nerve cells. Blood cells include, e.g., leukocytes, such as neutrophils, lymphocytes, monocytes, eosinophils, basophils, macrophages.

Methods for detecting the presence of bound ligands on the array surface may be chosen from a wide variety of detection techniques, including, for example, marker-based techniques, where the analyte(s) or an analyte specific reagent is labelled, e.g., with a radiolabel, a chromophore, fluorophore, chemiluminescent moiety or a transition metal.

For many applications, detection may be performed with a biosensor. A biosensor is broadly defined as a device that uses a component for molecular recognition (for example a layer with immobilised antibodies) in conjunction with a solid state physicochemical transducer. Biosensors may be based on a variety of detection methods. Typically such methods include, but are not limited to, mass detection methods, such as piezoelectric, optical, thermo-optical and surface acoustic wave (SAW) device methods, and electrochemical methods, such as potentiometric, conductometric, amperometric and capacitance methods. With regard to optical detection methods, representative methods include those that detect mass surface concentration, such as reflection-optical methods, including both internal and external reflection methods, angle, wavelength or phase resolved, for example ellipsometry and evanescent wave spectroscopy (EWS), the latter including surface plasmon resonance (SPR) spectroscopy, Brewster angle refractometry, critical angle refractometry, frustrated total reflection (FTR), evanescent wave ellipsometry, scattered total internal reflection (STIR), optical wave guide sensors, evanescent wave-based imaging such as critical angle resolved imaging, Brewster angle resolved imaging, SPR angle resolved imaging, and the like. Further, photometric methods based on, for example, evanescent fluorescence (TIRF) and phosphorescence may also be employed, as well as waveguide interferometers.

One exemplary type of SPR-based biosensors is sold by Biacore AB (Uppsala, Sweden) under the trade-name BIACORE® and is used in the Example below. These biosensors utilize a SPR based mass-sensing technique to provide a "real-time" binding interaction analysis between a surface bound ligand and an analyte of interest.

A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instruments may be found in U.S. Pat. No. 5,492,840. The full disclosures of the above-mentioned U.S. patents are incorporated by reference herein.

In the following Example, various aspects of the present invention are disclosed more specifically for purposes of illustration and not limitation.

EXAMPLE

Instrumentation

A BIACORE® 3000 instrument (Biacore AB, Uppsala, Sweden) was used. BIACORE® instruments are based on surface plasmon resonance (SPR) detection at gold surfaces, and a micro-fluidic system is used for passing samples and running buffer through four individually detected flow cells (one by one or in series), with very high precision and with small sample volumes needed. As sensor chip was used Series S CM5 (Biacore AB, Uppsala, Sweden) which has a gold-coated surface with a covalently linked carboxymethyl-modified dextran polymer hydrogel. The output from the instrument is a "sensorgram" which is a plot of detector response (measured in "resonance units", RU) as a function of time. An increase of 1000 RU corresponds to an increase of mass on the sensor surface of approximately 1 ng/mm$^2$.

Preparation of Cell Samples

A431 human epidermoid carcinoma cell line (ATCC #CRL-2592) which overexpresses epidermal growth factor (EGF), and a human T-cell leukaemia Jurkat cell line (ATCC#CRL-10915) which does not express the EGF receptor were each grown in culture media. A431 cells were grown in DMEM/FCS and Jurkat cells in RPMI/Lglu/FCS. Jurkat cells were harvested after three days, and A431 cells when they were 90-100% confluent. A431 cells were detached using Versene (EDTA solution) at a 1:5000 dilution.

After washing with PBS (10 mM phoshate buffer pH 7.4 with 150 mM NaCl) and PBS containing 2% bovine serum albumin (BSA, Sigma A3059, Sigma-Aldrich, Missouri, USA), cells were serially diluted into microtiter well plates.

Assay for Cell Surface EGF

Mouse anti-EGFr antibody (obtained from Oncogene Science, Cambridge, Mass., USA) at a specific concentration of 5 nM, was added to each cell sample well and incubated for 30 minutes on a rocking plate. The plate was then centrifuged for three minutes at 1400 rpm. The supernatants were injected into the BIACORE® 3000 over sensor chip surfaces with rabbit anti-mouse IgG1 antibody (obtained from Biacore AB, BR-1000-55) immobilized (18400 RU) to detect free antibody in the supernatants, i.e., antibody that had not bound to cell surface EGF. Cell samples were injected for two minutes. Between cell sample injections the sensor surface was regenerated by an injection of 10 mM glycine-HCl at pH 1.2 for 10 seconds.

Figure 4:
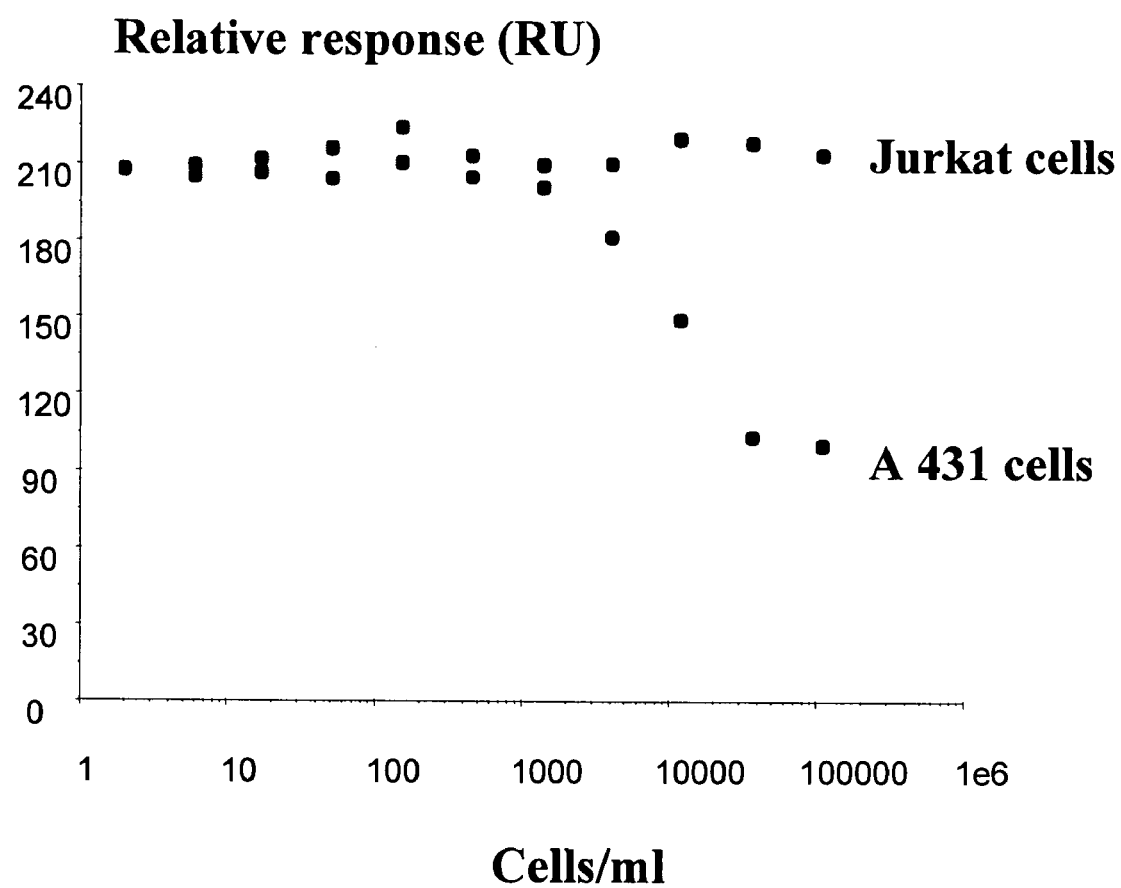
FIG. 4 is a diagram which shows detector response versus cell concentration at a sensor surface with immobilized anti-mouse IgG antibody for a fluid containing anti-EGF-antibody (at 5 nM concentration) after contact thereof with cells that do not express EGF-receptor (Jurkat cells) and cells that express EGF-receptor (A431 cells).

The results are shown in FIG. 4. As can be seen from the graph, the level of captured antibody when Jurkat cells were used was constant and independent of cell concentration. In contrast, the level of captured antibody was reduced when A431 cells were used and more so at higher cell concentration, reflecting that the antibody was partially bound to EGF-receptor on cell surfaces.

It is to be understood that the invention is not limited to the particular embodiments of the invention described above, but the scope of the invention will be established by the appended claims.

The invention claimed is:

1. A method for analysing a cell sample for the presence of cell surface-bound or intracellularly bound analytes, which method comprises of:
   (i) providing in at least one flow cell a solid support having thereon an array on a surface comprising thereof a plurality of different binding agents immobilized at defined positions on the surface, wherein each binding agent comprises one member of a specific binding pair;
   (ii) contacting the solid support array surface in the at least one flow cell with a set of different ligands each at a known concentration, each ligand comprising a first part capable of specifically binding to a specific analyte selected from cell surface-bound analytes and intracellularly bound analytes of a defined cell type, and a second part which comprises the other member of each specific binding pair, such that each ligand binds through its specific binding pair part to a specific position on the solid support surface whereupon the set of different ligands are passed in a laminar flow in the at least one flow cell;
   (iii) detecting the amount of binding of each ligand to the solid support array surface;
   (iv) incubating a cell sample-containing fluid, which contains cell fragments and intact cells, the membranes of the intact cells having been made permeable to ligands, with a set of ligands identical to that in step (ii), each ligand at the same concentration as in step (ii), to permit the ligands to bind to cell surface-bound or intracellularly bound analytes;
   (v) passing in a laminar flow the cell sample-containing fluid from step (iv) with a solid support surface according to step (i) to permit ligands that have not bound to cell surface-bound or intracellularly bound analytes to bind to the solid support surface; and
   (vi) detecting the amount of binding of each ligand to the solid support array surface obtained in step (v) and comparing that binding amount with the amount of binding of the same ligand obtained in step (iii), reduced binding in step (v) indicating the presence of ligand-specific cell surface-bound or intracellularly bound analytes in the cell sample.

2. The method according to claim 1, wherein the same solid support array surface is regenerated after step (iii), and is reused in step (v).

3. The method according to claim 1, wherein steps (v) and (vi) are repeated.

4. The method according to claim 1, wherein binding to the solid support surface is detected by a label-free detection method.

5. The method according to claim 4, wherein the detection method is based on mass-sensing.

6. The method according to claim 5, wherein the mass sensing comprises evanescent wave sensing.

* * * * *